United States Patent
Bennarsten

(10) Patent No.: US 6,640,807 B2
(45) Date of Patent: Nov. 4, 2003

(54) HIGH FREQUENCY OSCILLATION VENTILATOR

(75) Inventor: Johan Bennarsten, Gustavsberg (SE)

(73) Assignee: Siemens Elema AB, Solna (SE)

( * ) Notice: Subject to any disclaimer, the term of this patent is extended or adjusted under 35 U.S.C. 154(b) by 261 days.

(21) Appl. No.: 09/766,572

(22) Filed: Jan. 23, 2001

(65) Prior Publication Data

US 2001/0020473 A1 Sep. 13, 2001

(30) Foreign Application Priority Data

Mar. 9, 2000 (SE) ................................................ 0000777

(51) Int. Cl.[7] ................................................. A62B 9/02
(52) U.S. Cl. .................................. 128/205.24; 251/212
(58) Field of Search ........................ 128/200.24, 203.12, 128/204.18, 204.21, 205.24, 204.22, 104.23, 204.26, 205.18, 207.14–207.18; 251/12, 35, 42, 205, 212

(56) References Cited

U.S. PATENT DOCUMENTS

| | | | | |
|---|---|---|---|---|
| 5,555,880 A | * | 9/1996 | Winter et al. ........... | 128/204.21 |
| 6,042,573 A | * | 3/2000 | Lucey ...................... | 604/246 |
| 2001/0003984 A1 | * | 6/2001 | Bennarsten et al. ... | 128/204.21 |
| 2001/0009152 A1 | * | 7/2001 | Bennarsten ............ | 128/204.21 |

* cited by examiner

Primary Examiner—Glenn K. Dawson
(74) Attorney, Agent, or Firm—Schiff Hardin & Waite

(57) ABSTRACT

A high frequency oscillator (HFO) ventilator has an oscillator unit for alternately supplying a volume of gas ("oscillator volume") to and removing the oscillator volume from a proximal end of a gas conduit at a predetermined high frequency. The gas conduit has a proximal end connectable to the oscillator unit and a distal end connectable with the patient's airways. Located between the proximal end and the distal end is an inlet for receiving a continuous flow of a bias gas from a supply, and an outlet. The ventilator further has a flow controller adapted to apportion, between the distal end of the conduit and the outlet, the volume of gas supplied by the oscillator unit to establish a predetermined inspiration tidal volume for delivery to the patient's airways independent of the oscillator volume.

5 Claims, 2 Drawing Sheets

HIGH FREQUENCY OSCILLATION VENTILATOR

BACKGROUND OF THE INVENTION

1. Field of the Invention

The present invention relates to a high frequency oscillator (HFO) ventilator of the type in which high frequency pressure oscillations around a mean airway pressure are induced in a respiration gas to move small volumes of gas in to and out of a patient's airways in order to provide full ventilation support.

2. Description of the Prior Art

For HFO ventilation, it is known to provide an oscillator unit for alternately supplying a as volume to and removing a gas volume from a proximal end of a gas conduit (oscillator volume) at a predetermined high frequency, the gas conduit having a proximal end connectable to the oscillator unit and a distal end connectable with the patient's airways and, between the proximal end and the distal end of the conduit, to provide an inlet for bias gas and an outlet through which gas is removed from the conduit. The outlet typically includes a variable flow resistance which, together with a suitable flow rate of bias gas, establishes a mean airway pressure for gas within the conduit which is selected to open the lungs sufficiently to achieve an optimum gas transfer. The gas pressure within the conduit is then caused to oscillate around this mean by the alternate supply and removal of gas by the oscillator unit. This causes a volume of gas to move through the distal end of the conduit and be alternately supplied to (inspiration tidal volume) and removed from (expiration tidal volume) the patient's airways.

A problem with such a known HFO ventilator is that it is relatively inflexible, since the inspiration and expiration tidal volumes are dependent on the oscillator volume. The oscillator volume therefore must be changed in order to change either of the tidal volumes. It is difficult to provide an oscillator unit in which the oscillation can may be varied with any great precision or speed.

In addition to establishing the mean airway pressure, the bias gas flow also flushes carbon dioxide ($CO_2$) through the outlet that is expired by the patient and drawn into the conduit as part of the expiration tidal volume, so as to prevent the $CO_2$ from being re-breathed. The rate at which the $CO_2$ is removed depends on the flow rate of bias gas through the conduit, from inlet to outlet.

A further problem with the known HFO ventilator is that in order to provide a variable bias gas flow rate the oscillator unit must be capable of providing a variable oscillator volume greater than the desired inspiration tidal volume. This is because as the bias flow rate increases the flow resistance at the outlet must be decreased in order to maintain a predetermined mean airway pressure. This results in a greater amount of the oscillator volume flowing through the outlet since its resistance is lowered compared with that at the distal end of the conduit. In order to maintain a desired inspiration tidal volume, the oscillator volume must be increased to exceed this inspiration tidal volume.

SUMMARY

An object of the present invention is to provide an HFO ventilator which allows the inspiration tidal volume to be adjusted independently of the oscillator volume.

The above object is achieved in accordance with the principles of the present invention in an HFO ventilator of the type described above, which additionally includes a flow controller which divides the oscillator volume between the distal and the conduit and the outlet, thereby allowing the inspiration title volume to be selectively set, or the ratio of the inspiration title volume to the expiration title volume to be selectively varied.

The flow controller can be a size-variable restriction disposed within the conduit at a location between the inlet and outlet and the distal end of the conduit, for example in a common stem of a Y-piece connector, and which is operable to regulate the resistance to gas flow to and from the distal end of the conduit as the size is varied. Being located within the conduit enables the controller to be provided without significantly increasing the deadspace of the ventilator.

The HFO ventilator can have an oscillator unit that is capable of providing gross changes in the oscillator volume, for example providing a different maximum oscillator volume for use in ventilating different types of patients, such as adults, pediatric patients and neonates. In this embodiment the flow controller varies the tidal volume to suit the ventilatory requirements of individual patients within each category. This extends the operational range of the HFO ventilator without the need for accurate, and hence relatively expensive, oscillator volume control equipment.

DESCRIPTION OF THE PREFERRED EMBODIMENTS

Figure 1:
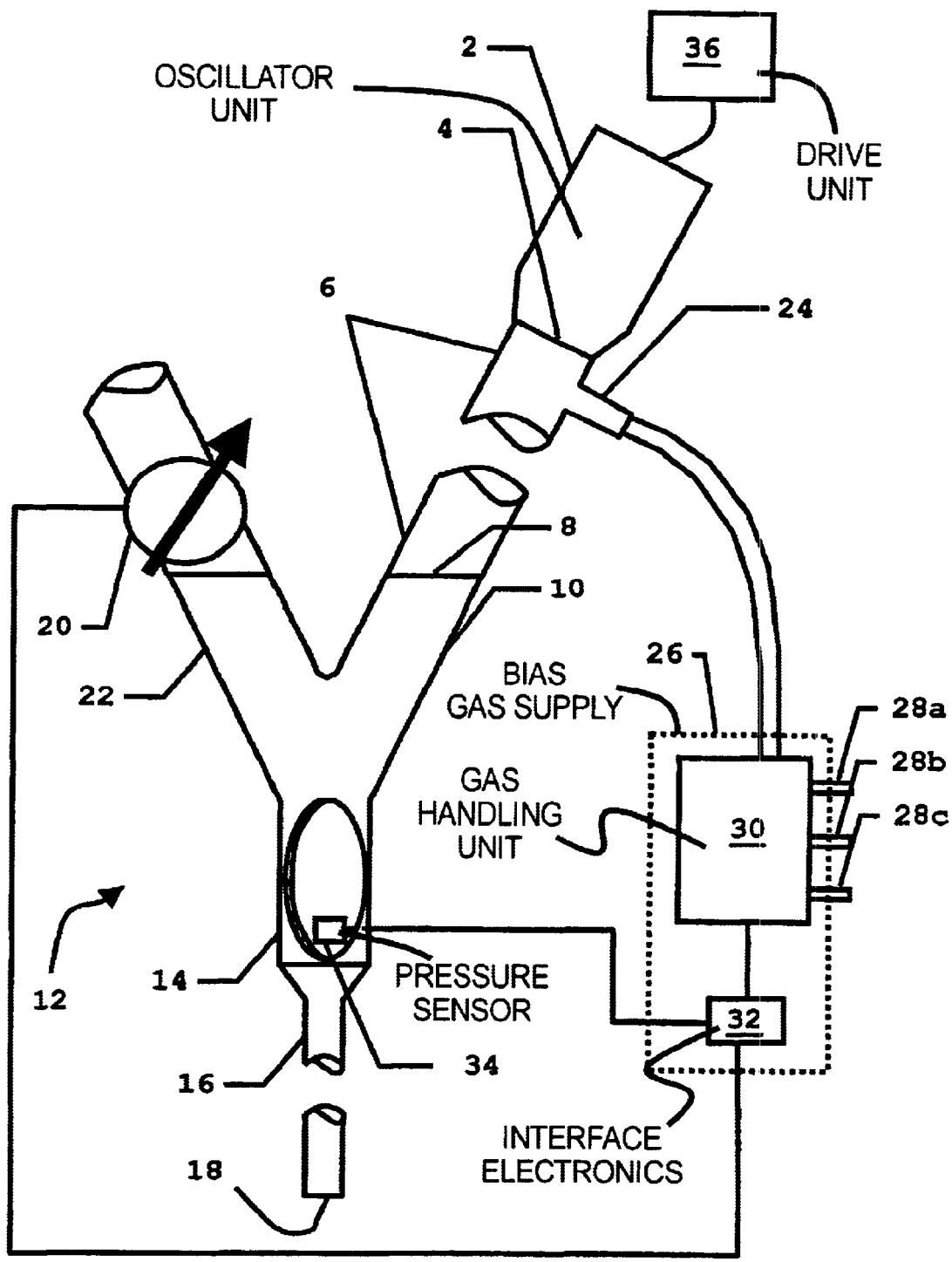
FIG. 1 is a schematic representation of a known HFO ventilator.

As shown in FIG. 1, a known HFO ventilator has an oscillator unit 2 connected to a first end 4 of a length of gas tubing 6 which is connected at a second end 8 to a first branch 10 of a Y-Piece connecting element 12. A common stem 14 of the Y-Piece 12 connects to an endo-tracheal tube 16 having an end 18 which intended for connection with a patient's airways. Thus the tubing 6, the first branch 10 and common stem 14 of the Y-Piece 12 and, optionally, the endotracheal tube 16, may be considered as forming a conduit having a proximal end 4 which is connected to the oscillator unit 2 and a distal end 18 which is intended for connection with a patient's airways. An adjustable flow resistance, such as a variable opening pressure mushroom valve 20, is connected to a second branch 22 of the Y-Piece 12 to provide an outlet for gas.

The gas tubing 6 is formed with an inlet 24 close to its first end 4 connected to a bias gas supply 26. The bias gas supply 26 is provided with one or more inlet ports (here illustrated as three) 28a, 28b and 28c for connection to one or more external pressurized gas sources (not shown). As is known in the art, the bias gas supply 26 may be a conventional mechanical ventilator modified to provide a continuous bias gas flow through the inlet 24. The bias gas supply 26 generally has a gas handling unit 30, functioning as a bias gas flow regulator, which receives gas from the external sources and conditions it (for example mixes the gases and controls the temperature and/or moisture content) to produce a breathing gas for supply into the tubing 6 as the bias gas. The bias gas supply 26 also generally includes control electronics 32 which may have a user interface (not shown) by which ventilator operating parameters are entered by a user and which controls the gas handling unit 30 to provide, inter alia, a desired bias gas flow and which also controls the opening pressure of the mushroom valve 20 so as to achieve a desired mean airway pressure. The mean airway pressure may be monitored a pressure sensor 34 within the conduit 6,10,14,16 which provides an output indicative of the airway pressure to the control electronics 32, where it is used to control the valve 20.

The known HFO ventilator also includes an oscillator drive unit 36 which typically drives an oscillator, such as a piston or a diaphragm, within the oscillator unit 2 at a selectable predetermined high frequency and stroke length to move a volume (oscillator volume) of breathing gas into and out of the tubing 6, to thereby induce high frequency pressure oscillations about the mean airway pressure which are transmitted from the proximal end 4 to the distal end 18 of the conduit 6,10,14,16. These oscillations in turn cause a volume of gas to move alternately into the patient's airways (inspiration tidal volume) and out of the patient's airways (expiration tidal volume). This volume is dependent on the oscillator volume.

Figure 2:
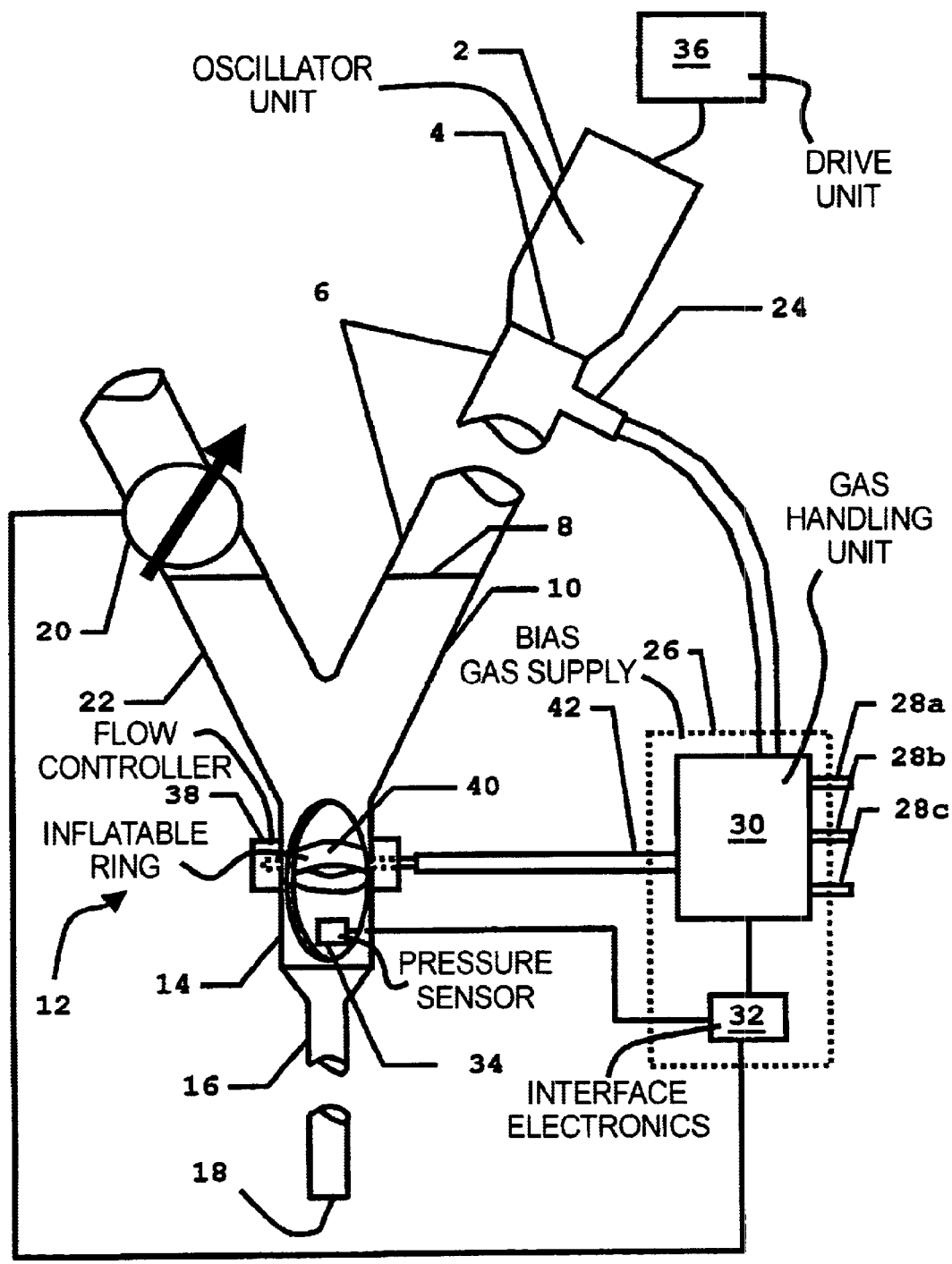
FIG. 2 is a schematic representation of an HFO ventilator according to the present invention.

The HFO ventilator according to the present invention is shown in FIG. 2, in which components common to the ventilator of FIG. 1 have identical reference numerals. In addition to the components of the known HFO ventilator, described above with respect to FIG. 1, a flow controller 38 is provided with a size-variable flow restriction, here in the form of a inflatable ring 40, disposed within the common stem 14 of the Y-Piece 12. A gas line 42 connects the ring 40 with the gas handling unit 30 which is controlled by the control electronics 32 to supply gas to and remove gas from the ring 40 as required. In this manner the resistance to gas flow between the distal end 18 of the conduit 6,10,14,16 and the branches 22,10 of the Y-Piece 12, and thus the inspiration and/or expiration tidal volumes, can be regulated by inflation and deflation of the ring 40.

In one mode of operation, the HFO ventilator of the present invention can be configured to facilitate the use of an adjustable bias flow without the need for varying the oscillator volume, as required by the known HFO ventilator. To do this the oscillator unit 2 is set to provide an oscillator volume of gas into the proximal end 4 of the tubing 6 that is sufficient to provide a desired inspiration tidal volume when the ring 40 is partially inflated and when the bias flow rate from the supply 26 is set at a known intermediate level. The control electronics 32 is adapted to regulate the operation of both the valve 20 and the flow controller 38 dependent on the flow and pressure readings output from the sensor 34 in order to maintain a predetermined mean airway pressure and inspiration tidal volume. Thus as the bias flow rate is increased the valve 20 must be regulated to lower its resistance to through flow so that the desired mean airway pressure can be maintained. In the known HFO ventilator, having an oscillator unit 2 capable of providing only a fixed oscillator volume would result in a greater fraction of the oscillator volume flowing through the valve 20 and a proportionate decrease in the inspiration tidal volume. In the HFO ventilator according to the present invention the sensor 34 detects a decrease in flow which causes the control electronics 32 to operate the gas handling unit 30 so as to deflate the ring 40. The resistance to gas flow toward the distal end 18 of the endotracheal tube 16 decreases and so the inspiration tidal volume can be maintained at a desired level. Clearly, if the gas handling unit 30 were operated to decrease the bias flow through the inlet 24, then the ring 40 would need to be inflated to maintain its resistance to flow relative to that of the valve 20.

In other modes of operation of the HFO ventilator according to the present invention, the ring 40 can be inflated or deflated in order to provide a desired inspiration tidal volume, for example entered via the user interface of the control electronics 32 as an operating parameter, or to vary the ratio of inspiration tidal volume to expiration tidal volume, without the need for an oscillator unit 2 which can produce a size-variable oscillator volume.

Although modifications and changes may be suggested by those skilled in the art, it is the intention of the inventors to embody within the patent warranted hereon all changes and modifications as reasonably and properly come within the scope of their contribution to the art.

I claim as my invention:

1. A high frequency oscillator ventilator comprising:

a gas conduit having a first end, and a second end adapted for connection to a patient's airways;

an oscillator unit connected to the first end of the gas conduit for alternating supplying a gas volume to, and removing a gas volume from, said first end of said gas conduit;

an inlet for bias gas disposed between said first and second end of said conduit;

an outlet disposed between said first and second ends of said conduit and cooperatively arranged with said inlet to delimit a bias gas flowpath; and a flow controller in communication with said gas conduit for apportioning, between said second end of said gas conduit and said outlet, the volume of gas supplied by said oscillator unit to establish a selectable inspiration tidal volume for delivery to the patient's airways, said flow controller comprising a size-variable restriction disposed within said gas conduit between said inlet and said second end of said gas conduit, said size-variable restriction being operable for regulating a resistance to gas flow between said first and second ends of said gas conduit as the size of said size-variable restriction is varied.

2. A high frequency oscillator ventilator as claimed in claim 1 further comprising a bias gas supply connected to said bias gas inlet, and a bias gas flow regulator which regulates a bias gas flow rate through said bias gas inlet, and a control unit for varying the size of the size-variable restriction dependent on said bias gas flow rate.

3. A high frequency oscillator ventilator as claimed in claim 1 comprising a gas flow sensor which monitors a gas flow parameter inside said gas conduit, said gas flow sensor being disposed between said flow controller and said second end of said gas conduit, said gas flow sensor producing a sensor output indicative of said gas flow parameter, and a control unit connected to said flow senior for receiving said sensor output therefrom for varying the size of the size-variable restriction dependent thereon to establish said tidal volume.

4. A high frequency oscillator ventilator as claimed in claim 1 wherein said gas conduit has a first branch connected to said oscillator unit, a second branch connected to said outlet, and a common stem connected to said first branch and to said second branch and adapted for connection to a patient's airways, said size-variable restriction being disposed in said common stem.

5. A high frequency oscillator ventilator as claimed in claim 1 wherein said flow controller apportions, between said second end and said outlet of said gas conduit, a volume of gas removed from said gas conduit by said oscillator unit to establish a selectable ratio of said inspiration tidal volume to an expiration tidal volume.

* * * * *